(12) United States Patent
Valori et al.

(10) Patent No.: US 10,247,684 B2
(45) Date of Patent: Apr. 2, 2019

(54) NUCLEAR MAGNETIC RESONANCE (NMR) DISTRIBUTIONS AND PORE INFORMATION

(71) Applicant: SCHLUMBERGER TECHNOLGOY CORPORATION, Sugar Land, TX (US)

(72) Inventors: Andrea Valori, Dammam (SA); Mohammed Badri, Al-Khobar (SA); Reza Taherian, Missouri City, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 341 days.

(21) Appl. No.: 15/027,389

(22) PCT Filed: Sep. 25, 2014

(86) PCT No.: PCT/US2014/057439
§ 371 (c)(1),
(2) Date: Apr. 5, 2016

(87) PCT Pub. No.: WO2015/053952
PCT Pub. Date: Apr. 16, 2015

(65) Prior Publication Data
US 2016/0245764 A1    Aug. 25, 2016

Related U.S. Application Data

(60) Provisional application No. 61/889,805, filed on Oct. 11, 2013.

(51) Int. Cl.
*G01N 24/08* (2006.01)
*G01N 15/08* (2006.01)
(Continued)

(52) U.S. Cl.
CPC .......... *G01N 24/081* (2013.01); *E21B 49/00* (2013.01); *G01N 15/088* (2013.01); *G01V 3/32* (2013.01); *E21B 43/20* (2013.01); *G01R 33/448* (2013.01)

(58) Field of Classification Search
None
See application file for complete search history.

(56) References Cited

U.S. PATENT DOCUMENTS

2003/0034777 A1\* 2/2003 Chen .................... G01V 3/32
324/303
2004/0027122 A1\* 2/2004 Heaton ................ G01N 24/081
324/303

(Continued)

OTHER PUBLICATIONS

Capitani, D. et al., "Metabolic Profiling and Outer Pericarp Water State in Zespri, CI.GI, and Hayward Kiwifruits", Journal of Agricultural and Food Chemistry, 2013, 61(8), pp. 1727-1740.

(Continued)

*Primary Examiner* — Jermele M Hollington

(57) ABSTRACT

For a given medium, a property may be inferred based on nuclear magnetic resonance (NMR) data. NMR data that includes two or more different NMR signals are used. Differences between any particular two of the two or more different NMR decays are computed and a distribution is produced based on the computed differences. The property of the medium may be inferred using the produced distribution. The produced distribution features the change in a parameter. The NMR distributions may be $T_2$ distributions, $T_1$ distributions, diffusion, or any other type of NMR data. The NMR data may be acquired: at different times, for different levels of invasion, before and after water flooding, or for different saturation states. The inferred property may pertain to the oil and gas industry, material analysis, medicine, pharmaceuticals, the process industry, or the food (Continued)

industry. For example, the inferred property may be the porosity of a subsurface formation.

20 Claims, 5 Drawing Sheets

(51) Int. Cl.
E21B 49/00 (2006.01)
G01V 3/32 (2006.01)
G01R 33/44 (2006.01)
E21B 43/20 (2006.01)

(56) References Cited

U.S. PATENT DOCUMENTS

| | | | |
|---|---|---|---|
| 2010/0010744 A1* | 1/2010 | Prange | G01V 3/32 |
| | | | 702/7 |
| 2010/0088033 A1* | 4/2010 | Chen | G01N 24/081 |
| | | | 702/8 |
| 2011/0025324 A1* | 2/2011 | Fransson | G01N 24/081 |
| | | | 324/307 |
| 2014/0184220 A1* | 7/2014 | Paulsen | G01N 24/081 |
| | | | 324/309 |
| 2014/0320126 A1* | 10/2014 | Heaton | G01V 11/00 |
| | | | 324/303 |
| 2015/0153433 A1* | 6/2015 | Paulsen | G01N 24/081 |
| | | | 324/309 |

OTHER PUBLICATIONS

Mactavish J. C. et al., "Hydration of White Cement by Spin Grouping NMR", Cement and Concrete Research, 1985, 15(2), pp. 367-377.

Mitchell, J. et al., "Mapping oil saturation distribution in a limestone plug with low-field magnetic resonance", Journal of Petroleum Science and Engineering, 2013, 108, pp. 14-21.

Sanderlin, A. B. et al, "Biofilm Detection in Natural Unconsolidated Porous Media Using a Low-Field Magnetic Resonance System", Environmental Science & Technology, 2013, 47(2), pp. 987-992.

She, A. M. et al., "Hydration Dynamics of Portland Cement Studied by Magnetic Resonance", Applied Mechanics and Materials, 2012, 193-194, pp. 509-512.

Zhang, J. et al., "Application of MRI to Monitor the Process of Navel Orange Ripening", Applied Mechanics and Materials, 2012, 220-223, pp. 1329-1334.

* cited by examiner

NUCLEAR MAGNETIC RESONANCE (NMR) DISTRIBUTIONS AND PORE INFORMATION

CROSS-REFERENCE TO RELATED APPLICATIONS

This application claims, under 35 U.S.C. § 119, priority to and the benefit of U.S. Provisional Patent Application No. 61/889,805, filed Oct. 11, 2013.

BACKGROUND

Nuclear Magnetic Resonance (NMR) tools used for well-logging or downhole fluid characterization measure the response of nuclear spins in formation fluids to applied magnetic fields. NMR tools typically have a DC magnet that produces a static magnetic field at a desired test location (e.g., where the fluid is located). The static magnetic field produces a magnetization in the fluid. The magnetization is aligned along the direction of the static field. The magnitude of the induced magnetization is proportional to the magnitude of the static field. A transmitter antenna produces a time-dependent radio frequency magnetic field that has a component perpendicular to the direction of the static field. The NMR resonance condition is satisfied when the radio frequency is equal to the Larmor frequency, which is proportional to the magnitude of the static magnetic field. The radio frequency magnetic field produces a torque on the magnetization vector that causes it to rotate about the axis of the applied radio frequency field. The rotation results in the magnetization vector developing a component perpendicular to the direction of the static magnetic field. At resonance between the Larmor and transmitter frequencies, the magnetization is tipped to the transverse plane (i.e., a plane normal to the static magnetic field vector). A series of radio frequency pulses are applied to generate spin echoes that are measured with the antenna.

NMR measurements can be used to estimate, among other things, sample porosity. For example, the area under the curve of a T2 distribution for a NMR measurement can be equated to or at least provides an estimate of the NMR-based porosity. The T2 distribution may also resemble the pore size distribution in water-saturated rocks. The raw reported porosity is provided by the ratio of the initial amplitude of the raw decay and the tool response in a water tank. This porosity is independent of the lithology of the rock matrix.

SUMMARY

For a given medium, a property may be inferred based on nuclear magnetic resonance (NMR) data. NMR data that includes two or more different NMR signals are used. Differences between any particular two of the two or more different NMR decays are computed and a distribution is produced based on the computed differences. The property of the medium may be inferred using the produced distribution. The produced distribution features the change in a parameter. The NMR distributions may be $T_2$ distributions, $T_1$ distributions, diffusion, or any other type of NMR data. The NMR data may be acquired: at different times, for different levels of invasion, before and after water flooding, or for different saturation states. The inferred property may pertain to the oil and gas industry, material analysis, medicine, pharmaceuticals, the process industry, or the food industry. For example, the inferred property may be the porosity of a subsurface formation.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. Embodiments are described with reference to the following figures. The same numbers are generally used throughout the figures to reference like features and components.

DETAILED DESCRIPTION

Figure 1:
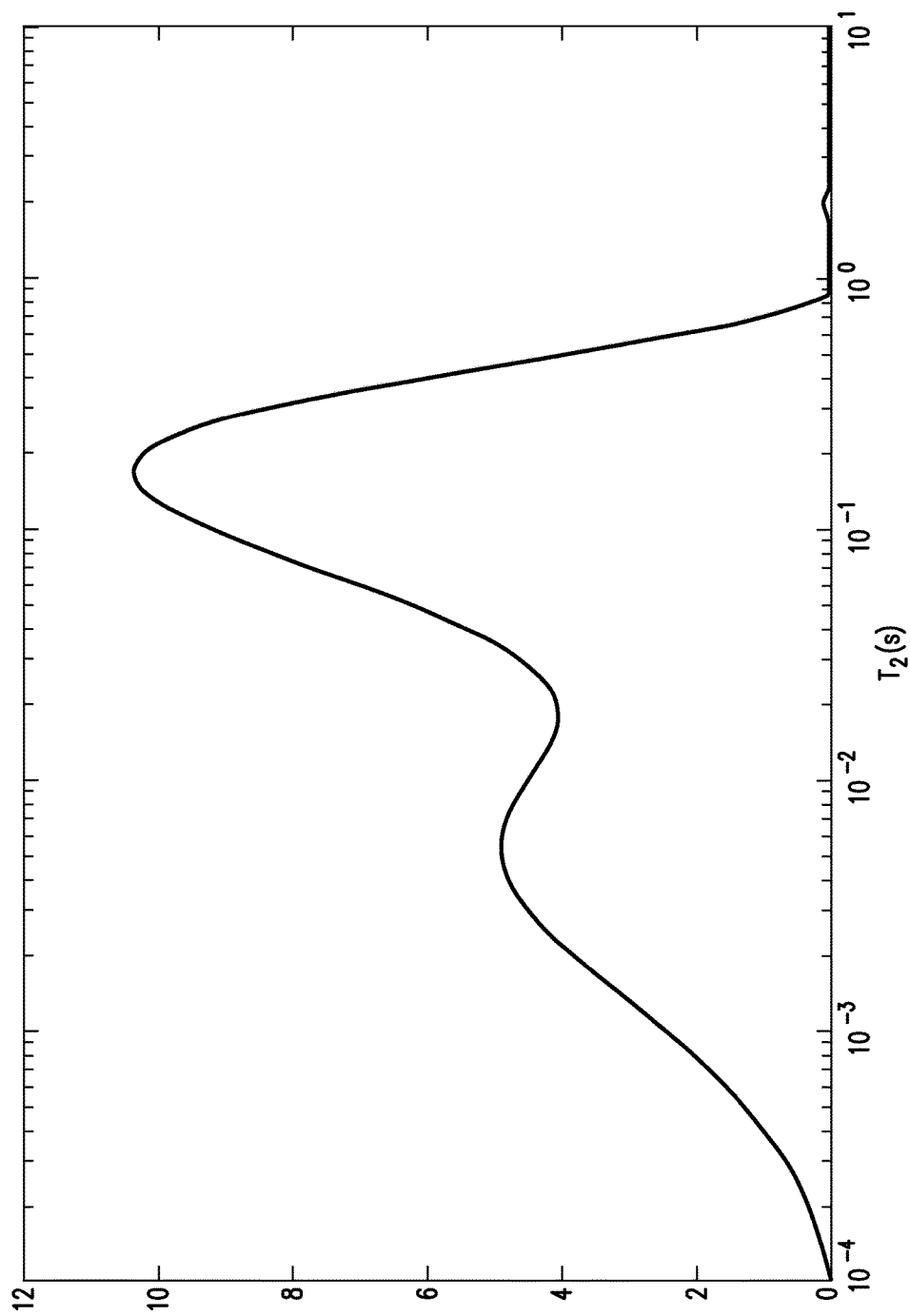
FIG. 1 is a plot showing the $T_2$ distribution of a fully water saturated rock sample.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Some embodiments will now be described with reference to the figures. Like elements in the various figures may be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used here, the terms "above" and "below", "up" and "down", "upper" and "lower", "upwardly" and "downwardly", and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship, as appropriate. It will also be understood that, although the terms first, second, etc. may be used herein to describe various elements, these elements should not be limited by these terms. These terms are only used to distinguish one element from another.

The terminology used in the description herein is for the purpose of describing particular embodiments only and is not intended to be limiting. As used in the description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

NMR $T_2$ distributions are commonly interpreted as pore size distributions. Shorter $T_2$s are considered as originating from smaller pore sizes in which the spins can quickly come into contact with paramagnetic impurities on the wall and lose their magnetization. In contrast, the spins in larger pores take a longer time to reach the wall and lose their magnetization. As a result, the $T_2$ decay time is dependent on the size of pores, although attempts to quantify this dependence have not been very successful. The most direct measure of pore size distribution is a mercury injected capillary pressure (MICP) measurement that is generally accepted as accurate. Many authors have tried to correlate the shapes of $T_2$ distributions to MICP measurements, with occasional success. In most cases, however, the two curves do not even have the same number of peaks. Extracting a pore size distribution out of a NMR $T_2$ distribution is an active area of research. This has proved difficult at least partly because the NMR data is first inverted using a regularization scheme that tends to smooth the outcome. Regularization and smoothing of the $T_2$ distribution limit the resolution to which the pore size can be extracted from the NMR data. Pores of "similar" size are merged in a unique peak in the $T_2$ distribution. $T_2$ distributions are often used as a monitoring tool on core plugs undergoing laboratory studies (for example, changes in saturation or aging). The limited resolution on the $T_2$ axis, however, sometimes makes it difficult to spot differences among the $T_2$ distributions.

Often it is desirable to compare two different $T_2$ distributions, but the relatively low resolution of these distributions makes it difficult to do so. For example, when a porous sample undergoes drainage or imbibition and NMR data are recorded at different stages, one may wish to investigate the variations in the NMR responses at the different stages (in addition to the shapes of the $T_2$ distributions). A system and method to better identify and resolve variations among different members of a family of $T_2$ distributions are described herein. Differences may be calculated in the time domain (i.e., differences of the CPMG train) and a Laplace inversion may be performed on the differences to obtain a $T_2$ distribution of the differences. This distribution is referred to herein as "$\Delta T_2$". One embodiment described herein is for $T_2$ distributions obtained during desaturation with air from fully water-saturated conditions, but can equivalently be applied to rocks undergoing other processes (such as aging) and on different types of data (e.g., $T_1$ distributions, diffusion, or any decaying data).

Reservoir rock formations are made of pores that contain the fluids (act of being a reservoir) and help fluid flow within the formation (act of being conduits). The pores, however, are not simple structures. The pores generally have a size distribution that spans a very wide range of values. The pore size distribution plays a major role in how pores act as a reservoir and as a conduit. The larger pores have the potential of being filled with hydrocarbons and thus are of great interest to the oil and gas industry. The larger pores generally are also better conduits: the reservoir fluids in those pores can flow more easily and are produced during the phase known as primary recovery. Once the primary recovery is over, there is about 70 to 80% of the initial oil volume remaining in smaller pores, and those smaller pores become of prime interest. Producing from the smaller size pore structures presents its own technical challenges. Most actions taken at this stage are based on what is known about the nature of those pores, the type of fluid in the pores, and further detailed information about the pores such as wettability, connectivity, and permeability. Thus, it is important to know what pores are involved during different phases of oil production from a reservoir.

NMR data is often acquired under different conditions. For example, when a well is originally drilled, logging-while-drilling (LWD) NMR tools can measure the NMR response of a formation before invasion (of drilling fluid filtrate into the formation) has taken place. Later on, perhaps several days later, wireline NMR tools may be used to perform the same measurements. Any such tool used may carry a processor to control operation of the tool and to store information in memory. During the intervening time between the two measurements, the formation has experienced some fluid changes. Invasion, which had only a minor contribution to the fluid composition and distribution at the time of the LWD measurement, has proceeded to full extent and has altered the fluid composition, and perhaps, the fluid distribution in the pore space of the rock. A wealth of information about the fluid composition and distribution exists in the two data sets and can be extracted by comparing them Another example is when the formation goes through water flooding. Before the water flooding starts, the formation has a certain NMR response resulting from the in situ fluid saturation. In most cases the in situ fluid consists of a combination of oil and water. Once the water flood starts and reaches the same measurement volume for which the first NMR measurement was recorded, the formation fluid becomes predominantly water, and to some extent residual oil. Thus, the NMR response before and after the water flood may be quite different. Those differences carry information about the subset of pores that contributed to water flood movement, and comparing the two NMR responses helps one parse the information about those pores from the obtained data.

Alternatively, the pores may not have been altered by the water flooding or invasion, and that can be useful information as well since those pores may still contain hydrocarbons. New strategies may need to be designed to extract the hydrocarbons from those pores. This frequently occurs in pores having an average diameter less than one micrometer and are filled with oil.

Standard NMR processing inverts for proton-containing fluids and provides, for example, a $T_2$ distribution. By further measurement and processing, that distribution may be separated into oil and water content. When the NMR tool makes a measurement, it provides an echo signal intensity, $S(t)$, which decays as a function of time. The echo intensity is proportional to the magnetization and the time dependence of magnetization decay, $S(t)$, is given by:

$$S(t) = \sum_i A_i \exp(-t/T_{2i}) \qquad (1)$$

where $S(t)$ is the echo signal intensity from the NMR tool and $A_i$ is the amplitude of (i.e., porosity associated with) the corresponding transverse relaxation time ($T_{2i}$). The relation in Eq. (1) is a sum of exponential decays that reflect the underlying assumption that the spins are subdivided into a number of subsets, each subset decaying exponentially with a decay constant $T_{2i}$. Each subset is typically a collection of spins in similar environments such as the same pore size, for example. A common practice in NMR logging is to invert the data ($S(t)$) using an inverse Laplace transform to obtain a set of $T_2$s and their corresponding $A_i$s, which can be plotted to generate the so-called $T_2$ distributions. Some examples of $T_2$s are shown in FIG. 1.

The data of FIG. 1 are for a fully water saturated rock sample and shows contributions from all pores in the structure of the rock sample used. The $T_2$ distribution of FIG. 1 is bimodal with a large peak originating from large pores, a smaller peak due to small pores, and a trough in between that may be attributed to the bound water cut off for this particular rock. It is common to visually compare these plots to decipher some useful information, but this is rather subjective and not a quantitative analysis.

Figure 2:
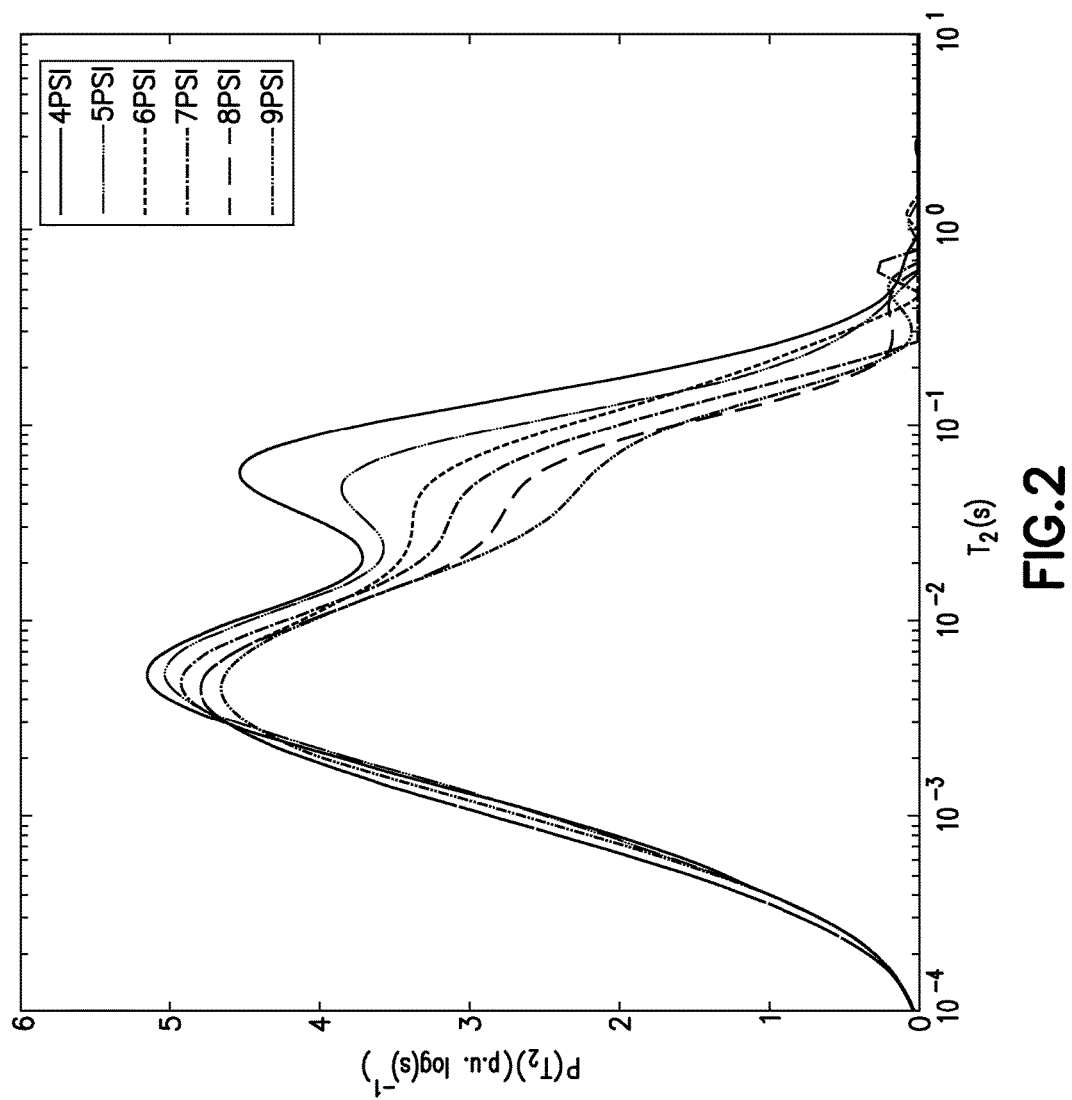
FIG. 2 is a plot showing $T_2$ distributions for a rock core plug at different saturation stages, in accordance with the present disclosure.

FIG. 2 illustrates the $T_2$ distribution of the same core plug as in FIG. 1, but at six intermediate water saturations. The intermediate saturations have been attained by spinning the sample in a centrifuge at different rotational speeds. The centrifugal force from spinning the sample is equivalent to injecting a fluid (air in this example) into the rock with certain pressure. Although a centrifuge was used to generate the data of FIG. 2, the saturation change happens in many instances, such as in water flooding the reservoir, invasion of mud filtrate, or changing the pressure or temperature of the reservoir, causing dissolved gas to evolve (bubble out), etc. The data in FIG. 2 corresponds to rotational speeds corresponding to pressures of four psi to nine psi. As the pressure increases, more of the water leaves the pore space of the sample as is evident from comparing the six data sets in FIG. 2. The pressures have been chosen close enough to demonstrate in detail, how the T2 distribution of the water that has not left the sample changes. However, the curves in FIG. 2 do not show the fluid that left the pore space.

To obtain the T2 distribution of the fluid that has left the rock, one can calculate a $\Delta T_2$ distribution which is described here. To be quantitative, first calculate $\Delta S$ for any two NMR decays, such as any two traces of FIG. 2, as:

$$\Delta S_{ij}(t) = S_j(t) - S_i(t) = \sum_k (A_{jk} - A_{ik})\exp(t/T_{2k}) = \sum_k \Delta A_k \exp(-t/T_{2k}) \qquad (2)$$

Note that the exponential term in the sum does not change between the $S_i$ and $S_j$. It is only the $\Delta A_k$ that are different. As a result, standard NMR inversion routines can be used to invert the data, but the output will be a set of $\Delta A$s rather than As. $A_s$ data can be inverted for $\Delta A$ at each $T_{2k}$ value. When plotted, this gives rise to a new type of distribution referred to herein as a $\Delta T_2$ distribution. If the pores contributing to one particular A, say $A_p$, are not perturbed by the operation (different pressure in this case) between the two measurements ($S_i$ and $S_j$), then $A_p$ is (substantially) the same for both measurements and $\Delta A_p$ is zero. This approach ensures that only pores that are perturbed between the two NMR measurements are represented in the resulting $\Delta T_2$ distributions.

Figure 3:
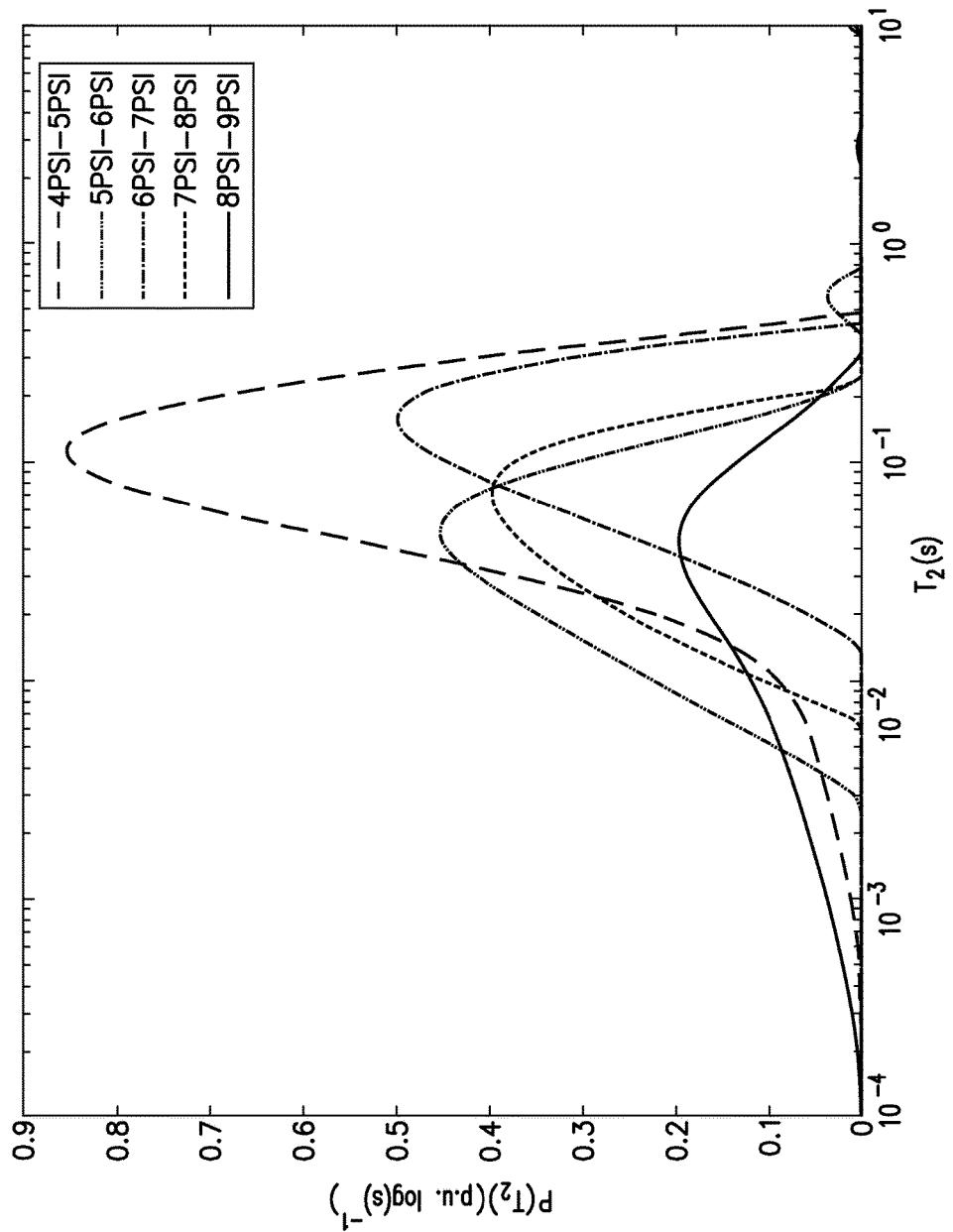
FIG. 3 is a plot showing $\Delta T_2$ distributions corresponding to the data shown in FIG. 2, in accordance with the present disclosure.

The resulting $\Delta T_2$ distributions have been plotted in FIG. 3. Note that the vertical scale changes from 10 porosity units (p.u.) in FIG. 2 to 4.5 p.u. in FIG. 3 and for most curves it is even smaller. This is expected since in the distributions plotted in FIG. 3 we are looking for the porosity change rather than the porosity itself.

Figure 4:
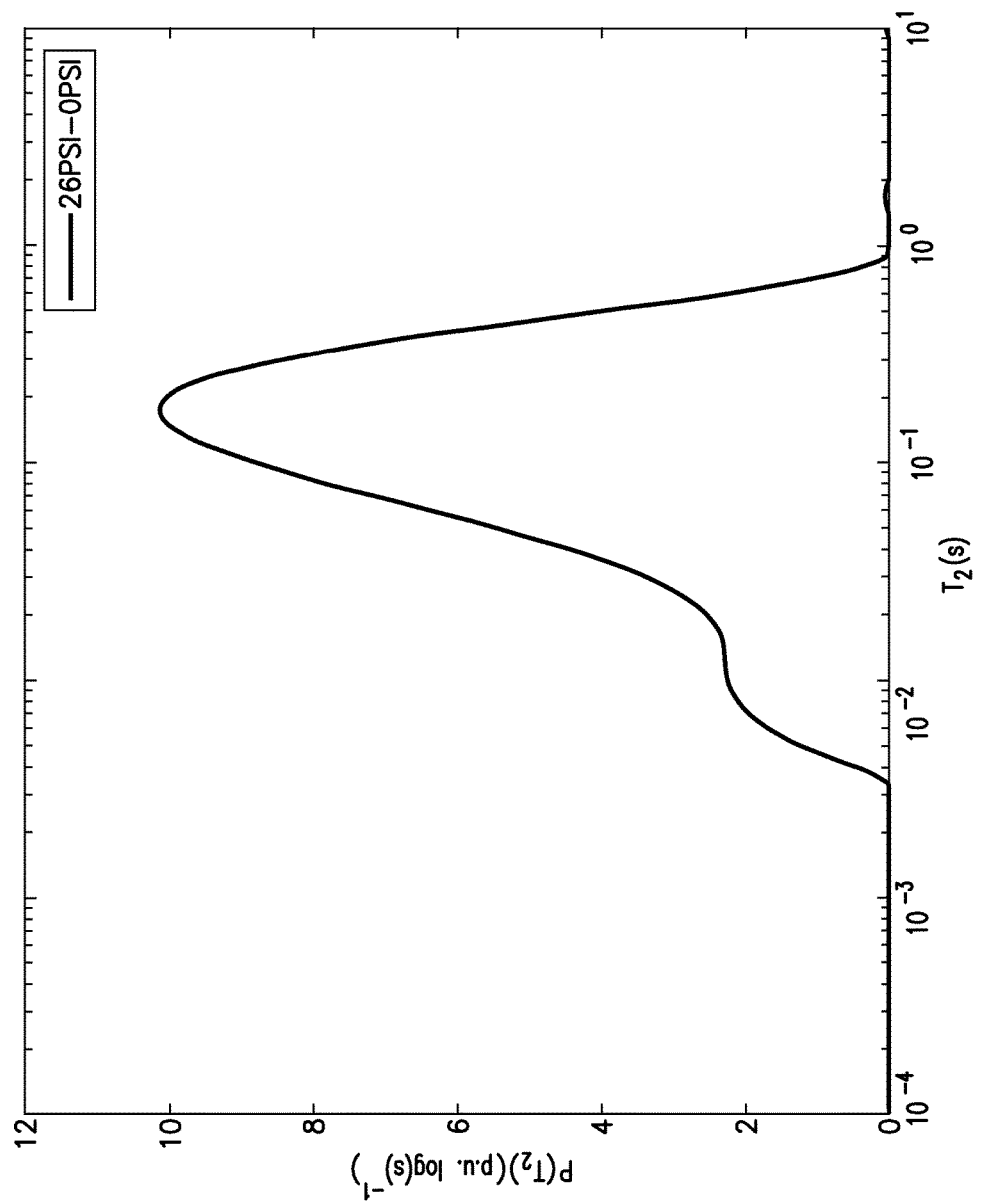
FIG. 4 is a plot showing $\Delta T_2$ distributions for two, non-adjacent pressure steps, in accordance with the present disclosure.

The technique can be applied to any two different saturation states. It is not limited, for example, to only slightly different perturbations (capillary pressures in this case). FIG. 4 shows the result for pressures of zero psi and 26 psi. A long list of perturbations exists that cause the spins to behave differently. This may include temperature change, pressure change, a change of one or more NMR measurement parameters (e.g., wait time, inter-echo spacing, gradient, etc.), changing the nature of the (pore) fluid (e.g., oil, water, gas, etc.), changing the characteristics of the pore wall (e.g., adding paramagnetic ions to or leaching some of the naturally occurring paramagnetic ions from the pore wall), etc. . . . .

Figure 5:
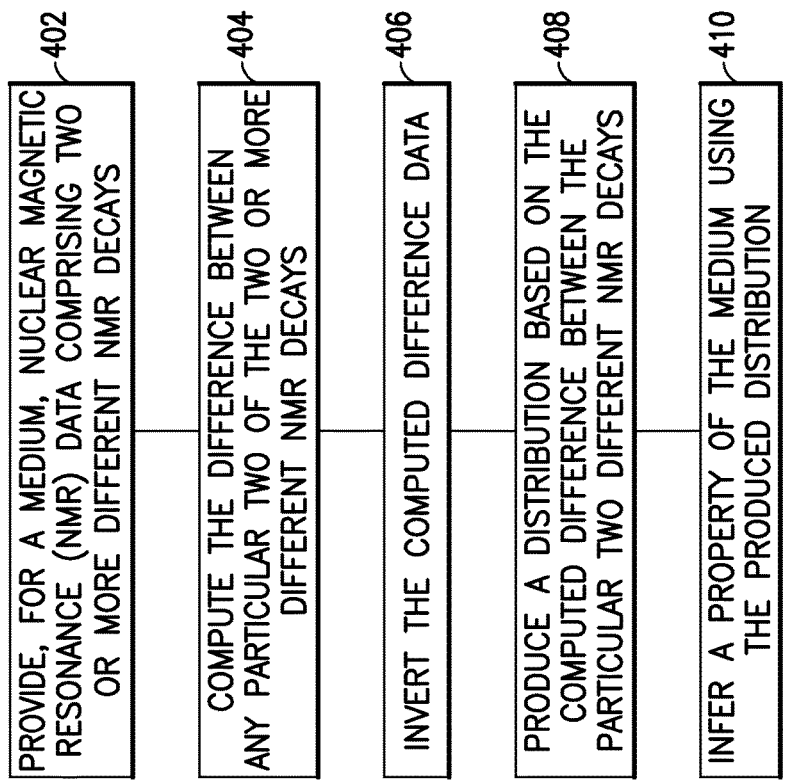
FIG. 5 is a workflow showing an embodiment of a produced NMR distribution, in accordance with the present disclosure.

FIG. 5 shows a workflow of an embodiment to produce a NMR distribution and infer a property of a medium, in accordance with this disclosure. The figure shows: providing, for a medium, nuclear magnetic resonance (NMR) data comprising two or more different NMR decays (402); computing the difference between any particular two of the two or more different NMR decays (404); inverting the computed difference data (406) and producing a distribution based on the inverted computed difference between the particular two different NMR decays (408); and inferring a property of the medium using the produced distribution (410).

Some of the methods and processes described above, including processes, as listed above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

While the embodiments described above particularly pertain to the oil and gas industry, this disclosure also contemplates and includes potential applications such as material analysis, medicine, pharmaceuticals, process industry, and the food industry.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions, and alterations herein without departing from the scope of the present disclosure.

The Abstract at the end of this disclosure is provided to comply with 37 C.F.R. § 1.72(b) to allow the reader to quickly ascertain the nature of the technical disclosure. It is submitted with the understanding that it will not be used to interpret or limit the scope or meaning of the claims.

While only certain embodiments have been set forth, alternatives and modifications will be apparent from the above description to those skilled in the art. These and other alternatives are considered equivalents and within the scope of this disclosure and the appended claims. Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method, comprising:
providing, for a medium, nuclear magnetic resonance (NMR) data comprising two or more different NMR signals;
computing the difference between any particular two of the two or more different NMR signals;
inverting the computed difference data;
producing a distribution based on the inverted computed difference between the particular two different NMR signals; and
inferring a property of the medium using the produced distribution;
wherein the NMR data comprising different NMR signals comprise NMR data acquired before and after water flooding.

2. The method of claim 1, wherein the NMR data are selected from the group consisting of $T_2$ distributions, $T_1$ distributions, diffusion, and any other type of NMR data.

3. The method of claim 1, wherein the computing the difference is done in the time domain and the producing the distribution based on the inverted computed differences is achieved by performing a Laplace inversion on the computed difference data.

4. The method of claim 1, wherein the NMR data comprising different NMR signals comprise NMR data acquired at different times.

5. The method of claim 1, wherein the NMR data comprising different NMR signals comprise NMR data acquired for different levels of invasion of drilling fluid into a formation comprising the medium.

6. The method of claim 1, wherein the NMR data comprising different NMR signals comprise NMR data acquired for different saturation states.

7. The method of claim 1, wherein the producing a distribution comprises inverting the computed difference and plotting the result.

8. The method of claim 1, wherein the produced distribution features the change in a parameter.

9. The method of claim 1, wherein the inferred property pertains to the oil and gas industry, material analysis, medicine, pharmaceuticals, process industry, or the food industry.

10. The method of claim 1, wherein the inferred property is the porosity of a subsurface formation.

11. The method of claim 1, further comprising identifying variations among different members of a family of distributions and resolving those variations.

12. The method of claim 1, further comprising identifying the types of pores involved during different phases of production from a reservoir.

13. A method, comprising:
providing, for a subsurface reservoir in a formation, different members of a family of nuclear magnetic resonance (NMR) distributions;
computing differences between particular members of the different family members;

obtaining a distribution of the differences;

determining a subset of pore size distribution and/or pore properties for the subsurface reservoir using the obtained distribution of the differences; and making decisions to manage the subsurface reservoir based on the determined pore size distribution;

wherein the NMR data comprising different NMR signals comprise NMR data acquired before and after fluid filtration into the formation.

14. The method of claim 13, wherein the NMR distributions are selected from the group consisting of $T_2$ distributions, $T_1$ distributions, diffusion, and any other type of NMR data.

15. The method of claim 13, wherein the computing differences is done in the time domain and the obtaining a distribution of the differences is achieved by performing a Laplace inversion on the computed differences.

16. The method of claim 13, wherein the obtained distribution of the differences features the change in a parameter.

17. The method of claim 13, further comprising determining the porosity of the subsurface reservoir.

18. The method of claim 13, further comprising identifying one or more pore types within the subsurface reservoir.

19. A non-transitory, computer-readable storage medium, which has stored therein one or more programs, the one or more programs comprising instructions, which when executed by a processor, cause the processor to perform a method comprising:

acquiring, for a medium, nuclear magnetic resonance (NMR) data comprising two or more different NMR signals;

computing the differences between any particular two of the two or more different NMR signals for various different NMR signals;

producing a distribution based on the inverted computed difference between the particular two different NMR signals; and inferring a property of the medium using the produced distribution;

wherein the NMR data comprising different NMR signals comprise NMR data acquired before and after water flooding.

20. The storage medium of claim 19, wherein the produced distribution based on the computed differences features the change in a parameter.

* * * * *